United States Patent [19]

Katner

[11] 4,304,774
[45] Dec. 8, 1981

[54] BIS-TETRAZOLMETHYL SUBSTITUTED β-LACTAM ANTIBIOTICS

[75] Inventor: Allen S. Katner, Indianapolis, Ind.

[73] Assignee: Eli Lilly and Company, Indianapolis, Ind.

[21] Appl. No.: 187,863

[22] Filed: Sep. 17, 1980

[51] Int. Cl.³ .................. A61N 31/535; C07D 498/04
[52] U.S. Cl. .......................... 424/248.51; 424/248.52; 542/418; 544/90
[58] Field of Search .......................... 544/90; 542/418; 424/248.51, 248.52

[56] References Cited

U.S. PATENT DOCUMENTS 4,138,486  2/1979  Narisada et al. ............... 424/248.52
4,226,866 10/1980  Christensen et al. .......... 424/248.51
4,232,151 11/1980  Nagata et al. .......................... 544/90

FOREIGN PATENT DOCUMENTS 2806457  8/1978  Fed. Rep. of Germany .

Primary Examiner—Henry R. Jiles
Assistant Examiner—Bernard Dentz

Attorney, Agent, or Firm—William B. Scanlon; Arthur R. Whale

[57] ABSTRACT

Broad spectrum β-lactam antibiotics represented by the formula

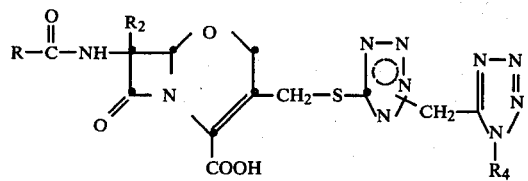

wherein R is the residue of a carboxylic acid, $R_2$ is H or $OCH_3$, and $R_4$ is hydrogen or $C_1$–$C_3$ alkyl; are obtained by reacting a 7-acylamino-3-halomethyl-1-oxa-β-lactam ester with the desired 1- or 2-tetrazolemethyl substituted 1H or 2H tetrazole-5-thiol. Alternatively, a 7-amino-3-halo-methyl-1-oxa-β-lactam ester is first reacted with the bis-tetrazole thiol and then the product is N-acylated with the desired carboxylic acid.

27 Claims, No Drawings 4,304,774

BIS-TETRAZOLMETHYL SUBSTITUTED β-LACTAM ANTIBIOTICS

BACKGROUND OF THE INVENTION

This invention relates to broad spectrum β-lactam antibiotic compounds. In particular, it relates to bicyclic 1-oxa-β-lactam compounds substituted in the 3-position with a bis-tetrazolmethyl thiomethyl substituent represented by the following general formula wherein the positions in the molecule are numbered as shown.

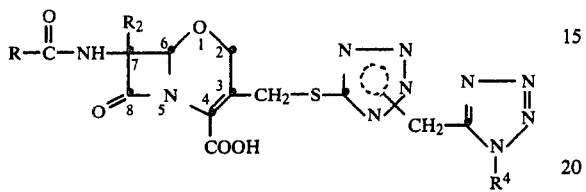

In the above formula, R represents the residue of a carboxylic acid, $R_2$ represents hydrogen or methoxy, and $R_4$ represents hydrogen or $C_1$–$C_3$ alkyl.

1-Oxa-β-lactam compounds are known, for example, those described in Belgium Pat. No. 863,998 issued May 29, 1978, and those described by Narisada et al., in U.S. Pat. No. 4,138,486, issued Feb. 6, 1979. In paricular, Narisada et al. describe 1-oxa-β-lactam compounds substituted in the 3-position with a 1-methyl-1H-tetrazol-5-yl-thiomethyl substituent, and in the 7-position with a phenylmalonamido substituent or an hydroxy or acyloxy substituted phenylmalonamido substituent. These 1-oxa-β-lactam compounds have high antibacterial activity and have stimulated numerous workers to carry out the synthesis of new members of the class with improved biological activity.

The compounds of this invention as represented by the above general formula differ structurally from those described by Narisada et al. U.S. Pat. No. 4,138,466, and in Belgium Pat. No. 863,998.

SUMMARY OF THE INVENTION

The 1-oxa-β-lactam antibiotics of this invention bear a bis-tetrazolmethyl substituent in the 3-position which is represented by the following structural formula A or B,

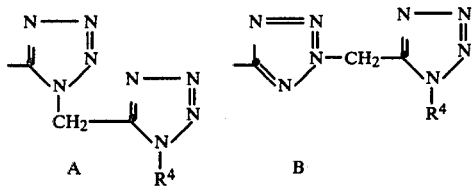

wherein $R_4$ represents hydrogen or $C_1$–$C_3$ lower alkyl.

The compounds are prepared by reacting a 7-acylamido-3-halomethyl-1-oxa-β-lactam with either a 1-(1H-tetrazol-5-ylmethyl)-1H-tetrazol-5-thiol or a 2-(1H-tetrazol-5-ylmethyl)-2H-tetrazol-5-thiol. Alternatively, a 7-amino-3-(bis-tetrazolmethyl thiomethyl)-1-oxa-β-lactam compound can be acylated with the desired carboxylic acid to provide a compound of the invention.

Compound of the above general formula wherein $R_2$ is methoxy are likewise prepared from the corresponding 7-methoxy compounds obtained by known methods.

The compounds of the invention are broad spectrum antibiotics which are particularly active against Proteus sp. and various strains of *H. influenzae*. The compounds are useful in the treatment and control of a wide variety of microorganisms pathogenic to man and animals when administered by the parenteral route.

DETAILED DESCRIPTION OF THE INVENTION

The 1-oxa-β-lactam compounds of this invention are represented by the following structural formula 1.

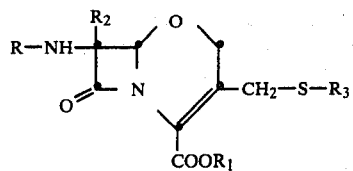

wherein R is hydrogen or an acyl group

wherein $R°$ is an aryl or aralkyl group of the formula

wherein $R^1$ is phenyl or phenyl substituted by halogen, hydroxy, amino, acetamido, $C_1$–$C_4$ alkyl, $C_1$–$C_4$ alkoxy, cyano, carboxy, carboxamido, carboxymethyl, $C_1$–$C_4$ alkoxycarbonylmethyl, hydroxymethyl, or aminomethyl, or $R^1$ is a di- or tri-substituted phenyl group of the formula

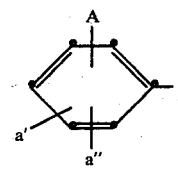

wherein each of a, a', and a" are independently hydrogen, halogen, hydroxy, $C_1$–$C_4$ alkyl or $C_1$–$C_4$ alkoxy; and n is 0 or 1;

or $R°$ is an aryloxymethyl or arylthiomethyl group

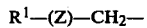

wherein $R^1$ has the same meanings as defined above and Z is O or S;

or $R°$ is a heterocyclic methyl group

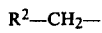

wherein $R^2$ is thienyl, furyl, 1H-tetrazol-1-yl, 1H-tetrazol-5-yl,

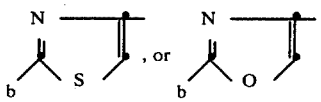

wherein each b is hydrogen, amino, protectedamino, C₁-C₃ alkyl or phenyl;
or R° is a group represented by the formula

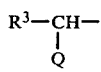

wherein R³ is R¹ as defined above and in addition 1,4-cyclohexadienyl, thienyl or furyl, and Q is hydroxy, carboxy, sulfo, or amino;
or R° is an oximino substituted group represented by the formula

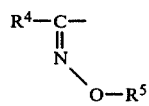

wherein R⁴ is R¹ as defined above and in addition thienyl, furyl, or

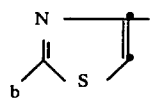

wherein b has the same meanings as defined above and R⁵ is hydrogen, or C₁-C₄ alkyl;
or R° is a group represented by the formula

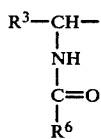

wherein R³ has the same meanings as defined above and R⁶ is phenyl substituted with from 1 to 3 hydroxy groups or pyridyl substituted with from 1 to 3 hydroxy groups;
or R⁶ is a group represented by the formula

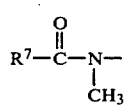

wherein R⁷ is C₁-C₄ alkylamino, phenyl, chlorophenyl, furyl, styryl, chlorostyryl, or nitrostyryl,
or R⁶ is a group represented by the formula

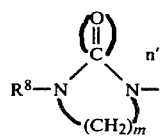

wherein n' is 1 or 2 and m is 2 or 3 with the limitation that when n' is 2, m is 2, and R⁸ is hydrogen, C₁-C₃ alkyl, C₂-C₄ alkanoyl, or C₁-C₃ alkylsulfonyl;
R₁ is hydrogen or a carboxy protecting group;
R₂ is hydrogen or methoxy;
R₃ is a bis-tetrazole methyl group represented by the formula

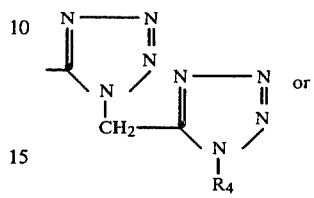

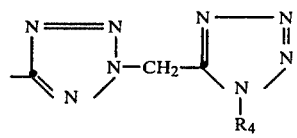

wherein each R₄ is hydrogen or C₁-C₃ alkyl; and
when R₁ is hydrogen, the pharmaceutically acceptable non-toxic salts thereof.

In the above definition of the compounds of the invention, the term "C₁-C₄ alkyl" refers to methyl, ethyl, n-propyl, iso-propyl, n-butyl, t-butyl, and the like; "C₁-C₄ alkoxy" refers to methoxy, ethoxy, t-butyloxy, n-propoxy, and the like; "C₁-C₄ alkoxycarbonyl methyl" refers to methoxycarbonylmethyl, ethoxycarbonylmethyl, iso-propoxycarbonylmethyl, and like esters of the carboxymethyl group.

When in the above formula 1, R¹ is a substituted phenyl group, illustrative examples of such groups are the halophenyl groups, for example, 4-chlorophenyl, 3-fluorophenyl, 4-bromophenyl, and like halophenyl groups; the hydroxyphenyl groups such as 4-hydroxyphenyl and 3-hydroxyphenyl; aminophenyl groups such as 2-aminophenyl and 4-aminophenyl; the acetamido substituted phenyl groups such as 4-acetamidophenyl and 3-acetamidophenyl; the C₁-C₄ alkylphenyl groups such as 4-methylphenyl, 4-ethylphenyl, 4-t-butylphenyl, and the like; the alkylphenyl ethers such as 4-methoxyphenyl, 3-methoxyphenyl, 3-ethoxyphenyl, 4-t-butoxyphenyl, 4-isopropoxyphenyl, 2-methoxyphenyl, and the like; the cyanophenyl groups such as 4-cyanophenyl; the carboxy substituted phenyl groups 2-carboxyphenyl and 4-carboxyphenyl; the carboxymethyl substituted phenyl groups, for example, 2-carboxymethylphenyl; the lower alkyl esters of the carboxymethyl substituted phenyl groups such as 4-ethoxycarbonylmethylphenyl; the hydroxymethylphenyl groups such as 2-hydroxymethylphenyl and 4-hydroxymethylphenyl; and the aminomethylphenyl groups such as 2-aminomethylphenyl.

Representative of the di- or tri-substituted phenyl groups for R¹ are 3,4-dichlorophenyl, 3,4-dihydroxyphenyl, 3-methyl-4-chlorophenyl, 3-hydroxy-4-chlorophenyl, 3-chloro-4-hydroxyphenyl, 3,5-dichloro-4-hydroxyphenyl, 3,5-dimethoxyphenyl, 3,4,5-trimethylphenyl, 2,6-dimethylphenyl, and like di- and tri-substituted phenyl groups.

Carboxy-protecting groups represented by the term R₁ in formula 1 are the well known ester forming groups used for the temporary protection of acidic carboxylic acid groups in other β-lactam antibiotics, for example, the penicillin and cephalosporin antibiotics. Examples of such groups which have general use are the arylmethyl groups, e.g. benzyl, p-methoxybenzyl, p-nitrobenzyl, diphenylmethyl (benzhydryl), 4-methoxydiphenylmethyl, and 4,4′-dimethoxydiphenylmethyl; the haloalkyl groups, e.g. 2-iodoethyl, and 2,2,2-trichloroethyl; the trialkylsilyl groups such as trimethylsilyl and triethylsilyl; alkyl groups e.g. t-butyl, and t-amyl; alkenyl groups e.g. allyl, 3-methylbut-1-ene-3-yl and 3-methylpent-1-ene-3-yl; and like carboxy protecting groups.

When the compound represented by the formula contains additional carboxylic acid groups in its structure, these carboxy groups also may be protected. For example, when Q is the formula 1 is carboxy, it also may be protected with an ester protecting group. Likewise, when $R^1$ is phenyl substituted by carboxy, this acidic group may be desirably protected.

Any free amino group substituents present in the compound of formula 1 are desirably protected during preparation. For example, a compound of the formula 1 wherein Q is amino, is protected during the acylation of a 3-(bis-tetrazolemethyl)-7-amino nucleus compound (formula 1, R=H) with an amino protected phenylglycine. Likewise, when the term $R^1$ is phenyl substituted by amino, the aromatic amino group is desirably protected during preparation of the compound of formula 1. The amino-protecting groups employed in the preparation of the compounds of the invention are conventional protecting groups. Illustrative of such groups are those commonly used in the $\beta$-lactam art such as those forming urethanes with the amino group, for example, t-butyloxycarbonyl, trichloroethoxycarbonyl and benzyloxycarbonyl; groups forming enamines, for example, methyl acetoacetate and ethyl acetoacetate; and arylmethyl protecting groups such as triphenylmethyl (trityl).

Any free hydroxy groups present in the compound of the invention can likewise be protected if needed. For example, the hydroxy group in compounds of the formula 1, wherein Q is hydroxy, or wherein $R^1$ is phenyl substituted by hydroxy, can be protected with conventional hydroxy protecting group. Labile ether forming protecting groups such as the ethers formed with dihydropyran, or methylvinyl ether are suitable for protecting phenolic hydroxy groups. For alkyl hydroxy groups, esters formed with the lower alkyl carboxylic acids such as formic, acetic or propionic, or such halogenated acids e.g. chloroacetic acid, dichloroacetic acid or $\beta,\beta$-dichloropropionic acid, are suitable protecting groups.

The following Table 1 lists illustrative examples of compounds represented by the above formula 1.

TABLE 1

| $R^\circ-\overset{\overset{O}{\|}}{C}-$ | $R_2$ | $R_3{}^1$ | $R_4$ |
|---|---|---|---|
| benzoyl | H | A | H |
| p-tolyl | OCH$_3$ | A | H |
| phenylacetyl | H | A | H |
| phenylacetyl | OCH$_3$ | A | H |
| phenylacetyl | OCH$_3$ | B | H |
| phenoxyacetyl | H | A | CH$_3$ |
| phenoxyacetyl | OCH$_3$ | A | H |
| phenylmercaptoacetyl | OCH$_3$ | B | H |
| 4-chlorophenylmercaptoacetyl | H | A | H |
| 2-thienylacetyl | H | B | H |
| 2-thienylacetyl | OCH$_3$ | A | CH$_3$ |
| 2-furylacetyl | OCH$_3$ | A | H |

TABLE 1-continued

| $R^\circ-\overset{\overset{O}{\|}}{C}-$ | $R_2$ | $R_3{}^1$ | $R_4$ |
|---|---|---|---|
| 2-amino-1,3-thiazol-4-ylacetyl | OCH$_3$ | B | H |
| 2-amino-1,3-thiazol-4-ylacetyl | OCH$_3$ | A | H |
| 2-amino-1,3-thiazol-4-ylacetyl | H | A | H |
| mandeloyl | H | A | H |
| mandeloyl | OCH$_3$ | A | H |
| O-formylmandeloyl | OCH$_3$ | B | H |
| α-sulfophenylacetyl | H | A | CH$_3$ |
| phenylglycyl | OCH$_3$ | A | H |
| phenylglycyl | OCH$_3$ | B | H |
| 2-thienylglycyl | H | A | CH$_2$CH$_3$ |
| α-amino-(1,4-cyclohexadiene-1-yl)acetyl | H | A | H |
| α-carboxyphenylacetyl | OCH$_3$ | A | H |
| α-methoxyimino-2-furylacetyl | OCH$_3$ | A | H |
| α-methoxyimino-2-furylacetyl | OCH$_3$ | A | CH$_3$ |
| α-methoxyimino-2-furylacetyl | OCH$_3$ | B | H |
| α-methoxyimino-α-(2-amino-1,3-thiazol-4-yl)acetyl | CH$_3$ | A | H |
| α-methoxyimino-α-(2-amino-1,3-thiazol-4-yl)acetyl | H | A | H |
| α-methoxyimino-α-(2-amino-1,3-thiazol-4-yl)acetyl | OCH$_3$ | B | H |
| α-(2,3-dihydroxybenzamido)phenylacetyl | H | A | CH$_3$ |
| α-(3-hydroxypyridin-(4-ylcarbonylamino)-phenylacetyl | OCH$_3$ | A | H |
| α-(3-cinnamoyl-3-methyl-1-ureido)-α-(4-hydroxyphenyl)acetyl | H | A | H |
| α-[3-(2-furoyl)-3-methyl-1-ureido]-α-phenylacetyl | OCH$_3$ | A | i-C$_3$H$_7$ |
| α-(3-methylcarbamoyl-3-methyl-1-ureido)-α-(4-hydroxyphenyl)-acetyl | OCH$_3$ | B | H |
| α-(3-methylcarbamoyl-3-methyl-1-ureido)-α-(4-hydroxyphenyl)-acetyl | H | A | H |
| α-(imidazolidin-2-one-1-ylcarbonylamino)-α-phenylacetyl | H | A | H |
| α-(imidazolidin-2-one-1-ylcarbonylamino)-α-phenylacetyl | OCH$_3$ | A | H |
| α-[3-(methylsulfonyl)-imidazolidin-2-one-1-ylcarbonylamino]-α-phenylacetyl | H | A | CH$_3$ |
| α-(4-ethylpiperazin-2,3-dione-1-ylcarbonyl- | | | |

TABLE 1-continued

| $\overset{O}{\underset{\|}{R°-C-}}$ | $R_2$ | $R_3$[1] | $R_4$ |
|---|---|---|---|
| amino)-α-phenylacetyl | H | A | H |

[1] A =

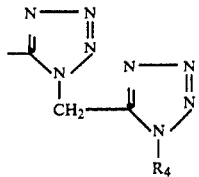

B =

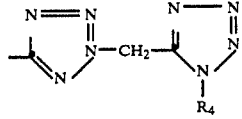

The compounds of the invention are formally named in a general manner as 7β-acylamido-7α-H or (7α-methoxy)-8-oxo-3-[1-(1H-tetrazol-5-ylmethyl)-1H-tetrazol-5-ylthiomethyl]-5-oxa-1-azabicyclo[4.2.0]oct-2-ene-2-carboxylic acids, and the correspondingly substituted compounds where in the 3-position the bistetrazole is a 2-(1H-tetrazol-5-ylmethyl)-2H-tetrazol-5-ylthiomethyl group, or a 1-(1H-tetrazol-5-ylmethyl)-1H-tetrazol-5-ylthiomethyl group.

Stereochemically, the 7-position side chain of the compounds of the invention has the β-configuration, while the methoxy group in the 7-position (when $R_2$=methoxy) has the α-configuration. When the 7-position side chain bears the substituent represented by the term "Q" in the formula 1, the asymmetric carbon atom can have either the D- or the L-configuration or a mixture of both. The D-configuration is preferred.

The compounds of the invention are prepared with the 3-halomethyl substituted compound represented by the following structural formula 2.

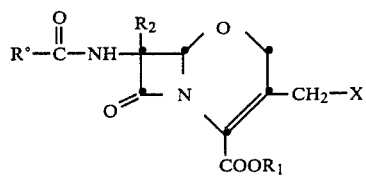

wherein R° and $R_2$ have the same meanings as defined above for the formula 1, $R_1$ is a carboxy protecting group, and X is chloro or bromo. Preferably, R° is phenyl or phenyl substituted with halogen, e.g. chloro; lower alkyl, e.g., methyl; or cyano.

The 3-halomethyl substituted compound is reacted with 1-(1H-tetrazol-5-ylmethyl)-1H-tetrazol-5-ylthiol or a $C_1$-$C_3$ alkyl derivative thereof represented by the formula 3,

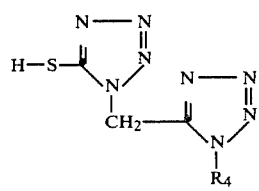

or a 2-(1H-tetrazol-5-ylmethyl)-2H-tetrazol-5-ylthiol or a $C_1$-$C_3$ alkyl derivative thereof represented by the formula 4,

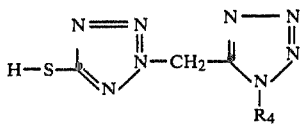

where in the above formulas 3 and 4, $R_4$ is hydrogen or $C_1$-$C_3$ alkyl. The reaction of the 3-halomethyl substituted 1-oxa-β-lactam with the thiol is carried out at a temperature between about 15° C. and about 55° C., preferably in a polar organic solvent such as dimethylformamide, dimethylacetamide, hexamethylphosphoramide (HMPA) or in a non-polar solvent, for example, a nitrile such as acetonitrile; or a halogenated hydrocarbon such as methylene chloride or a di- or trichloroethane. The reaction is carried out in the presence of a hydrogen halide acceptor, for example, pyridine or a trialkylamine such as triethylamine. Ordinarily, the commercial grades of dimethylformamide and dimethylacetamide contain sufficient free amine to scavenge the acid by-product. Preferably, the reaction is carried out in a two-phase system comprising a halogenated hydrocarbon solvent such as methylene chloride or dichloroethane, containing a quaternary salt such as tetra-n-butylammonium chloride, and an aqueous phase containing the bis-tetrazolmethyl thiol in dilute sodium hydroxide. When the reaction is complete, the organic phase containing the product is separated from the aqueous phase, is washed, and dried. The product can be recovered from the organic phase by evaporation.

The carboxylic acid group in the 4-position of the 3-halomethyl-1-oxa-β-lactam (Formula 2) is protected by esterification. Carboxy group protection during the reaction of the 3-halomethyl compound with the tetrazole thiols prevents the intramolecular lactone formation which can occur when the free carboxylic acid group is present.

The reaction can be carried out with equimolar amounts of the 3-halomethyl compound and the tetrazole thiol; however, better yields are obtained when an excess of the thiol is employed.

In an example of the preparation of a compound of the invention, p-nitrobenzyl 7β-phenylacetamido3-chloromethyl-1-oxa-β-lactam-4-carboxylate is reacted in dimethylformamide at a temperature between about 20° C. and about 35° C. with a 0.1 molar excess of 1-(1H-tetrazol-5-ylmethyl)-1H-tetrazol-5-thiol. The reaction mixture is stirred at the above temperature for about 12 hours, is then diluted with a mixture of water and ethyl acetate and the ethyl acetate layer is separated, washed with water and brine, and is dried over a drying agent such as sodium sulfate. Evaporation of the dried ethyl acetate affords the product which can be further purified by chromatography or crystallization.

Alternatively, the compounds of the invention as represented by the formula 1 can be prepared by acylating a 7β-amino-3-(bis-tetrazolmethylthiomethyl)-1-oxa-β-lactam ester or free acid represented by the following structural formula 5, -continued

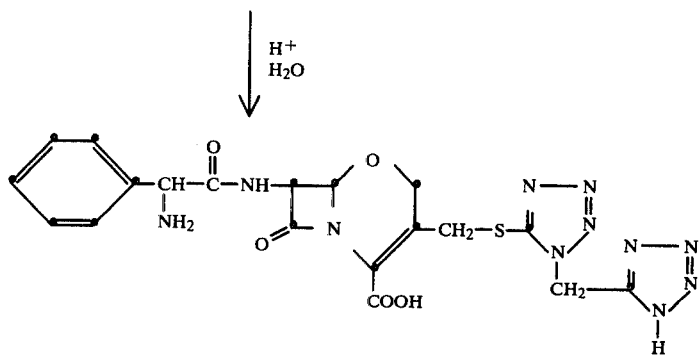

The t-butyloxycarbonyl group (t-BOC) and the trimethylsilyl ester group are removed upon treatment of the protected intermediate under acid hydrolysis conditions.

The compounds represented by the formula 1, wherein R is an acyl group represented by the formula

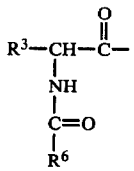

wherein $R^6$ is hydroxyphenyl or hydroxypyridyl, are prepared by acylating the α-amino group of a 7-phenylglycyl, thienylglycyl, or furylglycyl substituted 1-oxa-β-lactam represented by the formula 1 wherein R is an acyl group of the formula

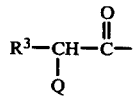

wherein Q is amino, with an active ester of the hydroxy substituted benzoic acid or the hydroxy substituted pyridine carboxylic acid. Preferably, the acylation is carried out by first preparing the hydroxybenzotriazole ester of the acid in the presence of a condensing agent such as a carbodiimide, for example, dicyclohexyl carbodiimide. The acylation of the phenylglycyl substituted compound of the formula 1 is carried out under non-aqueous conditions, for example, in dry THF or acetonitrile.

Representative of the hydroxy substituted benzoic acids and the hydroxy substituted pyridine carboxylic acids which can be employed are 4-hydroxybenzoic acid, 3-hydroxybenzoic acid, 2-hydroxybenzoic acid, 3-hydroxybenzoic acid, 2-hydroxybenzoic acid, 2,3-dihydroxybenzoic acid, 2,6-dihydroxybenzoic acid, and 3,4-dihydroxybenzoic acid, 3-hydroxypyridine-4-carboxylic acid, 2,3-dihydroxypyridine-4-carboxylic acid, 4-hydroxypyridine-3-carboxylic acid, 2,4-dihydroxypyridine-3-carboxylic acid, and 4,5-dihydroxypyridine-3-carboxylic acid.

An example of the preparation of the above hydroxy-substituted benzoic and hydroxy-substituted pyridine carboxylic acid derivatives is illustrated in the following reaction scheme in which 7-phenylglycylamino-3-[1-(1H-tetrazol-5-ylmethyl)-1H-tetrazol-5-ylthiomethyl]-1-oxa-4-carboxylic acid is reacted in acetonitrile with 2-hydroxybenzoic acid hydroxybenzotriazole ester to provide 7-[α-(2-hydroxybenzamido)-phenylacetamido]-3-[1-(1H-tetrazol-5-ylmethyl)-1H-tetrazol-5-ylthiomethyl]-1-oxa-4-carboxylic acid.

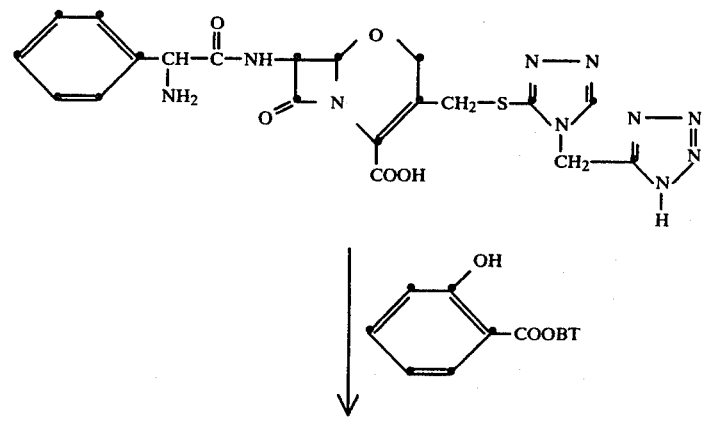

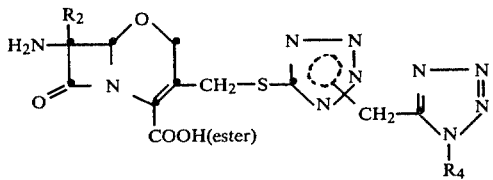

wherein R₄ has the same meanings as previously defined, and the bis-tetrazole substituent in the 3-position is a 1- or 2-substituted 1H- or 2H-tetrazole. The N-acylation of the 3-substituted nucleus compound represented by the formula 5 can be carried out by a variety of acylation methods. For example, the carboxylic acid forming the desired 7-acyl group can be coupled with the 7-amino nucleus in the presence of a dehydrating agent, for example, a diimide such as dicyclohexylcarbodiimide in an anhydrous organic medium to provide the N-acyl compound. Alternatively, an active derivative of the carboxylic acid can be used in the coupling reaction. Such active derivatives include the acid chlorides, acid bromides, acid azides, acid anhydrides, for example those formed with the acid $R^0$—C(=O)—OH and methyl chloroformate or iso-butyl chloroformate, or active esters such as those formed with hydroxybenzotriazole or hydroxysuccinimide. The N-acylation is best carried out in a non-aqueous medium, for example, in an organic solvent such as acetonitrile, tetrahydrofuran, dioxane, dimethylformamide, dimethylacetamide, nitromethane, or a halogenated hydrocarbon solvent such as methylene chloride or dichloroethane.

The acylation of the 3-substituted 7-amino nucleus compounds is carried out under non-aqueous conditions with an active derivative of the carboxylic acid. Generally, the carboxy group of the nucleus is protected during the acylation, for example, with a carboxylic acid protecting group. Suitable protecting groups include, for example, p-nitrobenzyl, p-methoxybenzyl, benzyl, diphenylmethyl, 2,2,2-trichloroethyl, t-butyl, and like ester groups which are easily cleaved under hydrolytic or hydrogenolytic conditions. Alternatively, the carboxy group of the 7-amino nucleus compound can be temporarily protected during the N-acylation as a silyl ester, for example, the trimethylsilyl ester formed by reacting a suspension of the free nucleus acid with a silylating agent such as trimethylsilyl acetamide or bis-trimethylsilyl acetamide.

Active derivatives of the carboxylic acid acyl moiety which can be employed in the acylation include, for example, the pentachlorophenyl ester, a mixed anhydride, for example, the mixed anhydride formed with methyl chloroformate or with isobutyl chloroformate; an active ester formed with N-hydroxysuccinimide or hydroxybenzotriazole (HBT); an acid halide or an acid azide.

The free acid itself can be coupled with the 7-amino nucleus compound in the presence of a condensating agent, for example, a carbodiimide such as dicyclohexylcarbodiimide.

The following illustrate the non-aqueous acylation method for the preparation of compounds of the formula 1.

7-Amino-3-[1-(1H-tetrazol-5-yl-methyl)-1H-tetrazol-5-ylthiomethyl]-1-oxa-β-lactam-4-carboxylic acid is reacted in acetonitrile with trimethylsilyl acetamide to form the trimethylsilyl ester of the 7-amino nucleus, and the nucleus ester is acylated with the mixed anhydride of an amino-protected phenylglycine formed with methyl chloroformate to provide the aminoprotected 7-phenylacetamido-3-[1-(1H-tetrazol-5-ylmethyl)-1H-tetrazol-5-ylthiomethyl]-1-oxa-β-lactam-4-carboxylic acid trimethylsilyl ester. The trimethylsilyl ester is hydrolyzed to the free acid and the amino protecting group is removed to provide the deprotected amino acid. The above is illustrated by the following reaction scheme wherein the t-butyloxycarbonyl group is the amino protecting group.

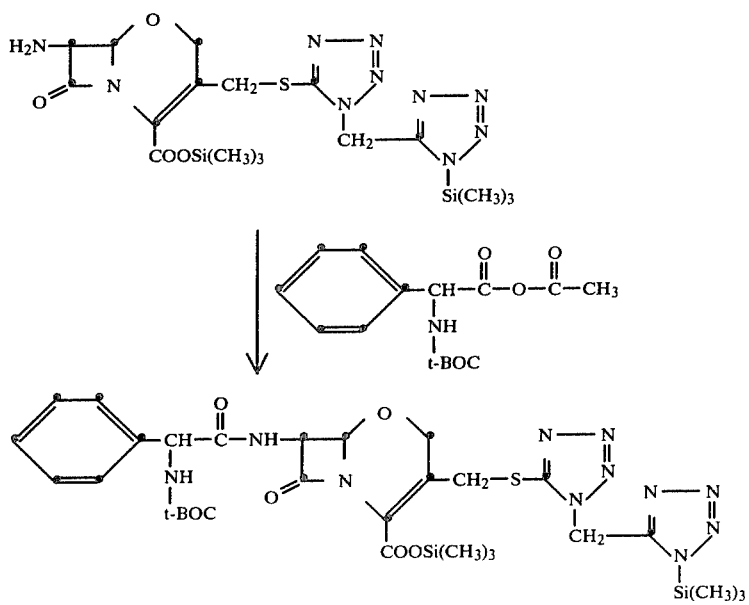

-continued

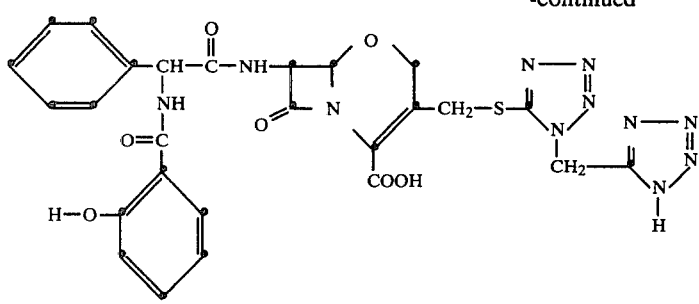

The compounds represented by the formula 1 wherein $R^6$ is a group of the formula

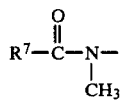

are prepared with a compound of the formula 1 wherein R is a phenylglycyl, furylglycyl, or thienylglycyl group represented by the term $R^3$—CH(Q)—C= wherein Q is amino. When in the above formula $R^7$ is phenyl, chlorophenyl, furyl, styryl, nitrostyryl, or chlorostyryl, the compounds are prepared by acylating the α-amino group of the phenylglycyl substituted 1-oxa-β-lactam with an N-chlorocarbonyl amide derivative represented by the following formula.

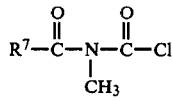

The N-chlorocarbonyl amides are prepared by reacting the N-methyl amide of the $R^7$-COOH acid with phosgene in an inert solvent in the presence of a hydrogen halide acceptor. Representative of the N-methyl amides which can be employed in the acylation are N-methylbenzamide, N-methyl-4-chlorobenzamide, N-methyl-3-chlorobenzamide, N-methyl-2-furoic acid amide, N-methyl-3-furoic acid amide, N-methylcinnamide, N-methyl-4-chlorocinnamide, N-methyl-4-nitrocinnamide, N-methyl-2-chlorocinnamide, and N-methyl-2-nitrocinnamide.

The N-methyl amide is reacted with phosgene in an inert solvent such as a chlorinated hydrocarbon solvent, for example, methylene chloride or trichloroethane in the presence of a hydrogen halide acceptor, for example, a tri-lower alkyl amine, for example, triethylamine or pyridine.

The N-chlorocarbonyl amides are coupled with the α-amino group of the 1-oxa compound via an N-acylation which can be carried out under aqueous or non-aqueous conditions in the presence of a hydrogen halide acceptor. The acylation is carried out at a temperature between about −5° C. and about 35° C. and preferably at about 0°–5° C. The solvents which can be employed in the acylation include acetonitrile, THF, DMF, and dimethylacetamide.

The compounds represented by the formula 1 wherein $R^7$ is a $C_1$–$C_4$ alkylamino group are likewise prepared by the acylation of the α-amino substituted compound represented by the formula 1 with an N-alkyl-N'-methyl-N'-chlorocarbonyl substituted urea.

For example, N,N'-dimethylurea is reacted with phosgene in an inert solvent to provide the N-chlorocarbonyl derivative which is then used in the acylation of the α-amino substituted 1-oxa-β-lactam under the acylation conditions described above. Representative of the N,N'-disubstituted ureas which can be used in the acylation to prepare compounds of the formula 1 are N,N'-dimethylurea, N-ethyl-N-methylurea, N-(n-butyl)-N'-methylurea and like N-($C_1$–$C_4$ alkyl-N'-methylureas.

The compounds represented by the formula 1 wherein $R^6$ is a group of the formula

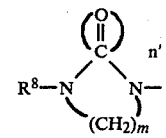

are prepared by acylating the α-amino group in a 7β-phenylglycylamino-1-oxa-β-lactam with N-chlorocarbonyl derivative of the formula

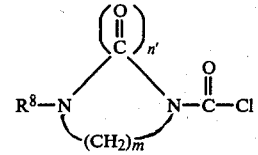

For example, N-chlorocarbonylimidololidin-2-one (n'=1, m=2) is reacted in acetonitrile, containing propylene oxide as the HCl scavenger, with the 7-phenylglycylamino-1-oxa-β-lactam of the formula 1 to provide the 7-[α-(imidazolidin-2-one-1-ylcarbonylamino)-phenylacetylamino]-1-oxa-βlactam.

Examples of cyclic ureas represented by $R^6$ which can be used to prepare the compounds of the invention are 4-ethylpiperazin-2,3-dione-1-ylcarbonyl chloride ($R^8$=ethyl, n'=2, m=2), 3-methylimidazolidin-2-one-1-ylcarbonyl chloride ($R^8$=methyl, n'=1, m=2), 3-acetylimidazolidin-2-one-1-ylcarbonyl chloride ($R^8$=acetyl, n'=1, m=2), and 3-methylsulfonylimidazolidin-2-one-1-ylcarbonyl chloride ($R^8$=methylsulfonyl, n'=1, m=2).

The 3-halomethyl-1-oxa-β-lactams (formula 2) employed in the preparation of the compounds of the invention are prepared according to the methods described in Belgium Pat. No. 863,998. Compounds of the formula 1 wherein $R^0$ is the group $R^3$—CH(Q)— and Q is a protected carboxy group are prepared as described by Narisada, et al., U.S. Pat. No. 4,138,486.

The 3-substituted 7-amino nucleus compounds represented by the formula 5 are prepared by the N-deacylation of an N-acyl 1-oxa-β-lactam represented by the formula 2, preferably wherein R⁰ is phenyl or a substituted phenyl group. The N-deacylation of the side chain acylamido group is carried out by the well known deacylation procedure employed to N-deacylate cephalosporin compounds which comprises the formation of an imido halide with a phosphorus halogenating agent such as phosphorus pentachloride, formation of the corresponding imino ether with the imino chloride and an alcohol such as methyl alcohol, and hydrolysis of the imino ether. For example, diphenylmethyl 7-benzamido-3-[1-(1H-tetrazol-5-ylmethyl)-1H-tetrazol-5-ylthiomethyl]-1-oxa-β-lactam-4-carboxylate is reacted in methylene chloride with phosphorus pentachloride at a temperature between about −15° C. and about 20° C. After imino chloride formation is complete, the reaction mixture is treated with methyl alcohol while the temperature is maintained at about −5° to about 0° C. The intermediate imino ether is then hydrolyzed by the addition of water to the reaction mixture. The 7-amino nucleus compound of the formula 5 is best isolated in the form of a salt, for example, the hydrochloride salt.

Alternatively the 7-amino nucleus compounds (formula 5) can be prepared in a manner analogous to the procedures used for preparing the 7-amino-1-oxa-β-lactam nucleus compounds described by U.S. Pat. No. 4,138,486.

A preferred group of compounds of this invention are represented by the formula 1 wherein R₃ is the bis-tetrazole represented by the formula A. An especially preferred group of compounds are represented by the formula 1 wherein R is an acyl group, R⁰—C(=O)— wherein R⁰ is a group of the formula R₃—CH(Q)—, and Q is carboxy or a carboxy protecting group. The preferred compounds are represented by the following structural formula.

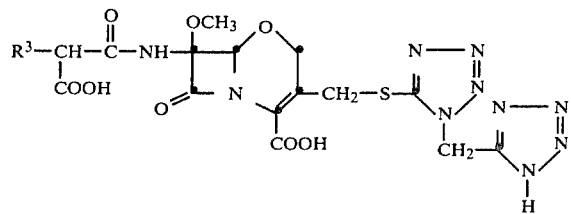

wherein R³ is phenyl or hydroxyphenyl.

An especially preferred compound of the invention is represented by the following structural formula.

tion, the 7-methoxy group has the α-configuration, and the asymmetric carbon in the 7-position side chain preferably has the D-configuration.

The carboxy group in the 4-position of the compounds of the invention is an acidic function which forms salts with inorganic and organic bases. Many of these salts are pharmaceutically acceptable salts, for example, the alkali metal salts such as the sodium and potassium salts, the alkaline metal salts such as the calcium salt, amine salts formed with pharmaceutically acceptable amines such as ethanolamines, for example, the mono, di, and triethanolamine salts, the ammonium salt, the salts formed with organic amines such as the lower alkyl mono, di, and trialkylamines, and cycloalkylamines, for example, the salts formed with dimethylamine, diethylamine, and dicyclohexylamine; and other amine salts such as those formed with abietyl amine or procaine. It will be recognized that compounds of formula 1 having a carboxy substituent in another portion of the molecule may form di salts, for example, the preferred compounds of the invention represented by the above formula can form di salts such as the disodium or dipotassium salt.

The compounds of the invention are useful in the control of microorganisms pathogenic to man and animals, and can be used in the treatment of infections caused by a variety of microorganisms when administered parenterally. For example, the compounds of the invention, and preferable a pharmaceutically acceptable non-toxic salt thereof, can be administered intravenously or intramuscularly. The compounds or pharmaceutically acceptable salts thereof can be formulated with suitable carriers for IM or IV administration. This invention also relates to pharmaceutical formulations comprising a compound of the formula 1 and a carrier. Suitable carriers include pharmaceutically acceptable diluents such as Water For Injection, physiologically saline, 5% dextrose, Ringer's solution, or a suitable oil such as ethyl oleate. The compounds of the invention, or a pharmaceutically acceptable non-toxic salt thereof, can be administered at a dose of between about 25 mg/kg and 500 mg/kg. Because of the variability in the factors affecting the disease state from patient to patient, the treatment regimen may vary. Such factors as the severity of the disease, the sensitivity of the infectious microorganism to the antibiotic, and the general state of the patient's health, may affect the course of treatment. For example, multiple doses may be given on a daily basis and the duration of treatment may vary from one week to two weeks or longer.

The following Table 2 contains the minimum inhibitory concentrations obtained in the agar dilution test with a preferred compound of the invention.

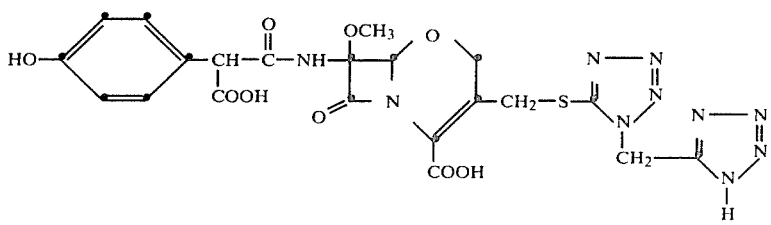

As described hereinabove, the 7-position side chain of the above preferred compounds has the β-configura-

TABLE 2

In Vitro Antibiotic Spectrum of

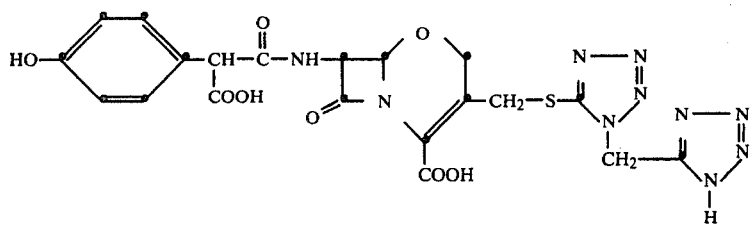

| Test Microorganism | Strain | mic (mcg/ml) |
|---|---|---|
| Staphylococcus aureus | Xl.1 | 32 |
| Staphylococcus aureus | V41 | 32 |
| Staphylococcus aureus | X400 | >128 |
| Staphylococcus aureus | S13E | 64 |
| Staphylococcus epidermidis | EPI1 | >128 |
| Staphylococcus epidermidis | EPI2 | >128 |
| Streptococcus A | C203 | 6 |
| Streptococcus pneumoniae | PARK | 64 |
| Strepcoccus D | X66 | >128 |
| Streptococcus D | 9960 | >128 |
| Haemophilus influenzae | C.L. | .03 |
| Haemophilus influenzae | 76 | .015 |
| Shigella sonnei | N9 | 1 |
| Escherichia coli | N10 | 8 |
| Escherichia coli | EC14 | 1 |
| Escherichia coli | TEM | 1 |
| Klebsiella sp. | X26 | 1 |
| Klebsiella sp. | KAE | 32 |
| Enterobacter aerogenes | X68 | 1 |
| Enterobacter aerogenes | C32 | 2 |
| Enterobacter aerogenes | EB17 | 2 |
| Enterobacter cloacae | EB5 | 64 |
| Enterobacter cloacae | 265A | >128 |
| Salmonella sp. | X514 | 32 |
| Salmonella sp. | 1335 | 32 |
| Pseudomonas aeruginosa | X528 | 32 |
| Pseudomonas aeruginosa | X239 | 16 |
| Pseudomonas aeruginosa | Ps18 | 8 |
| Serratia marcescens | X99 | 1 |
| Serratia marcescens | SE3 | 32 |
| Proteus morganii | PR15 | 16 |
| Proteus inconstans | Pr33 | .06 |
| Proteus rettgeri | PR7 | 64 |
| Proteus rettgeri | C24 | .03 |
| Citrobacter freundii | CF17 | 64 |
| Bordetella baronchoseptica | 16 | 128 |

The bis-tetrazolmethyl thiol compounds used in the preparation of the compounds of the invention are prepared as described in copending application serial No. 187,861, filed this even date. As described therein, 1-cyanomethyl-1H-tetrazol-5-ylthiol is reacted with tetramethylguanidinium azide in dioxane at the reflux temperature to provide the 1-(1H-tetrazol-5-ylmethyl)-1H-tetrazol-5-thiol. The corresponding 2H-tetrazole substituted tetrazole is obtained by alkylating 1H-tetrazole-5-thiol, wherein the thiol group is protected with a thiol protecting group such as the benzyl group, with a haloacetonitrile such as chloroacetonitrile in the presence of a base such as potassium or sodium hydroxide. The alkylation provides a mixture of 1- and 2-cyanomethyl-5-benzylthio-1H-tetrazoles. The isomeric mixture of the cyanomethyl substituted tetrazole is then reacted with tetramethylguanidinium azide or with aluminum triazide at elevated temperatures to provide a mixture of 1-(1H-tetrazol-5-ylmethyl)-1H-tetrazol-5-thiol and 2-(1H-tetrazol-5-ylmethyl)-2H-tetrazol-5-thiol wherein the thiol group is protected, for example, with a benzyl group. The isomeric mixture of the bis-tetrazoles is separated into the individual isomers via HPLC chromatography.

The $C_1-C_3$ alkyl substituted tetrazoles ($R_4=C_1-C_3$ alkyl) are obtained by alkylating the respective isomeric tetrazoles with a $C_1-C_3$ alkyl bromide or iodide in the presence of a base. The alkylation affords an isomeric mixture which can be separated into the individual isomers by HPLC chromatography. Following the separation of the individual isomeric tetrazoles or the alkylation products thereof as described above, the benzyl group is removed from the thiol by electrolytic reduction at a mercury pool cathode.

Alternatively, the 1-[1-($C_1-C_3$ alkyl)-1H-tetrazol-5-ylmethyl]-1H-tetrazol-5-thiol is prepared with ethyl 5-chloro-1H-tetrazol-1-acetate. The 5-chlorotetrazole acetate is reacted with a $C_1$–$C_3$ alkylamine to provide the corresponding N-($C_1$–$C_3$ alkyl)amide. The amide is then reacted with an excess of phosgene at a temperature of about −5° to about 10° C. in an inert solvent, for example, a halogenated hydrocarbon solvent such as methylene chloride or dichloroethane, to provide the corresponding N-chlorocarbonyl-N-($C_1$–$C_3$ alkyl)amide. The N-chlorocarbonylamide is then reacted with tetramethylguanidinium azide in dioxane at the reflux temperature to provide the 1-[1-($C_1$–$C_3$ alkyl)-1H-tetrazol-5-ylmethyl]-5-chloro-1H-tetrazole. The latter is then reacted with sodium hydrosulfide to replace the 5-chloro group with the thiol group.

The following examples further illustrate the invention.

In the following description of the preparation of the bis-tetrazolemethyl thiols and in the Examples, the abbreviations have the following meanings.

HPLC=High Performance Liquid Chromatography
NMR=nuclear magnetic resonance
UV=ultraviolet
IR=infrared
DMSO-$d_6$=deuterated dimethylsulfoxide In the description of the NMR spectra, s=singlet, m=multiplet, d=doublet, q=quartet, and t=triplet.

Preparation of Bis-tetrazolemethyl Thiols
1-Cyanomethyl-1H-tetrazol-5-ylthiol

A. Ethyl azidoacetate

To a solution of 490 g. (4 moles) of ethyl chloroacetate in 1500 ml. of acetonitrile were added 260 g. (4 moles) of sodium azide, and the mixture was heated at the reflux temperature for 20 hours. After heating, the reaction mixture was poured into 1 liter of water with stirring for ½ hour. The organic phase was separated from the aqueous phase and evaporated in vacuo to dryness. The yellow residual oil was dissolved in 1200 ml. of diethyl ether and the solution was dried over magnesium sulfate. Evaporation of the diethyl ether in vacuo gave 391 g. (76% yield) of ethyl azidoacetate.

B. Ethyl 5-chloro-1H-tetrazol-1-ylacetate

A mixture of 130 g. (1 mole) of ethyl azidoacetate prepared as described in part A and 96 g. (1.56 mole) of cyanogen chloride was heated at a temperature of 125° C. for 20 hours. After the reaction mixture had cooled, the reaction product mixture was dissolved in ethyl acetate, and the solution was filtered and evaporated in vacuo yielding a yellow crystalline mass of product. The yellow crystals were recrystallized from aqueous ethyl alcohol and gave 149 g. (78% yield) of ethyl 5-chloro-1H-tetrazol-1-ylacetate as pale yellow crystals melting at about 57°–60° C.

C. Ethyl 5-thiol-1H-tetrazol-1-ylacetate

A solution of 209 g. of the chlorotetrazole ester, prepared as described in part B above, and 250 g. of sodium hydrosulfide in 5 liters of ethyl alcohol was heated at the reflux temperature for 24 hours. After heating, the reaction mixture was acidified with concentrated hydrochloric acid, and the volume of the acidified mixture was reduced to ¼ the original volume by evaporation in vacuo. The concentrate was extracted with ethyl acetate, the extract was dried and evaporated to dryness under reduced pressure. The residual product was recrystallized from toluene-methylene chloride-hexane and gave 129 g. of the product melting at about 85° C. to 88° C.

D. 5-Thiol-1H-tetrazol-1-ylacetamide ammonium salt

A solution of 20 g. (0.106 mole) of the tetrazolthiol ester, prepared as described above in part C, in 320 ml. of concentrated ammonium hydroxide and 200 ml. of ethyl alcohol containing 500 ml. of ammonium chloride was heated at the reflux temperature for about 12 hours. After heating, the reaction mixture was evaporated in vacuo, and the yellow crystalline residue obtained was recrystallized from hot ethyl alcohol to yield a first crop of 13.7 g. (73% yield) of the product as white crystals melting at about 197° to about 199° C. after vacuum drying. A second crop of 1.4 g. of the product was obtained which melted at about 191°–193° C.

E. 1-Cyanomethyl-1H-tetrazol-5-thiol

A suspension of 5.28 g. of the tetrazolamide ammonium salt, prepared as described above in part D, in 90 ml. of methylene chloride containing 14.4 ml. of pyridine was cooled to a temperature of about 0° C. To the suspension was added dropwise with stirring a solution of 4.6 g. (30 mmole) of phosphorus oxychloride in 40 ml. of methylene chloride. After the addition was completed, the reaction mixture was heated at the reflux temperature for 30 minutes and was then cooled to room temperature with stirring. The reaction mixture had turned orange after heating and contained some precipitate. The reaction mixture was evaporated to dryness in vacuo and the residue dissolved in ethyl acetate-water, 1:1, v:v. The pH of the solution was adjusted to pH 2 with 20% aqueous hydrochloric acid. The acidified solution was then extracted twice with 75 ml. portions of ethyl acetate and the extracts combined. The extract was then washed with 5% hydrochloric acid, with brine, was dried over sodium sulfate and evaporated in vacuo. The brown oil obtained as a residue crystallized on standing. The crystals were vacuum dried at room temperature and yielded after drying 2.6 g. (61% yield) of light brown product melting at about 113°–114° C.

The above reaction was repeated on a 10.6 g. batch of the tetrazolamide ammonium salt and 3.7 g. of the nitrile as off-white crystals melting at about 116°–118° C. were obtained.

The following analytical data were obtained for the crystalline product.

Elemental analysis calcualted for $C_3H_3N_5S$: Theory: C, 25.53; H, 2.14; N, 49.62. Found: C, 25.82; H, 2.40; N, 49.91.

The mass spectrum of the crystalline product showed a molecular weight of 141 in agreement with the product.

1-(1H-Tetrazol-5-ylmethyl)-1H-tetrazol-5-thiol preparation

A solution of 6.0 g. (42.5 mmole) of 1-cyanomethyl-1H-tetrazol-5-thiol and 10.0 g. (6.3 mmole) of tetramethylguanidinium azide in 90 ml. of dioxane was heated at the reflux temperature for 3 hours. After cooling, the reaction mixture was evaporated to dryness in vacuo and the residue dissolved in ethyl acetate:water, 1:1. The ethyl acetate layer was separated, and the pH of the aqueous layer was adjusted to pH 1.8 with 20% hydrochloric acid. The acidified aqueous layer was then extracted 3 times with 75 ml. portions of ethyl acetate, and the extracts were combined. The extract was washed with 5% hydrochloric acid, with brine, was dried over sodium sulfate, and then evaporated in vacuo to dryness. The red oil obtained as a residue crystallized on seeding. The crystals were washed with ethyl acetate and with diethyl ether and were dried. There were obtained 3.7 g. of the bis-tetrazolmethyl thiol melting at about 173° C. to about 175° C. The filtrate from the first crop was evaporated to an oil and after seeding the oil, 0.3 g. of a second crop crystalline product were obtained. A third crop of 0.3 g. was obtained in the same manner. Total yield of product was 4.3 g. (55% yield).

The NMR spectrum of the product run in DMSO-$d_6$ showed a singlet at 5.9 ppm delta for the protons of the methylene group bridging the tetrazole rings.

1-(1-Methyl-1H-tetrazol-5-ylmethyl)-1H-tetrazol-5-thiol preparation

A. N-Methyl-5-chloro-1H-tetrazol-1-yl-acetamide

A solution of 19.5 g. (0.102 mole) of ethyl 5-chloro-1H-tetrazol-1-acetate in 30 ml. of ethyl alcohol was cooled in a dry ice-propyl alcohol bath, and methylamine gas was passed into the solution for 5 minutes. The reaction mixture solidified and was washed with ethyl alcohol and diethyl ether and was dried on the steam bath. There were obtained 13.2 g. (74% yield) of the N-methylamide product as white crystalline needles melting at about 146° to 148° C.

The following analytical data were obtained for the crystalline product.

Elemental analysis calculated for $C_4H_6N_5OCl$: Theory: C, 27.36; H, 3.44; N, 39.89; Cl, 20.19. Found: C, 27.59; H, 3.35; N, 39.65; Cl, 20.49.

NMR (DMSO-$d_6$): δ 2.7 (d, J=5 Hz, 3H, amide methyl), 5.28 s, 2H, $CH_2$), 8.53 (s, broad, 1H, N-H) ppm.

Molecular weight via mass spectrum=175.5

B. 1-(1-Methyl-1H-tetrazol-5-ylmethyl)-5-chloro-1H-tetrazole

To a suspension of 1.75 g. (10 mmole) of 5-chloro-N-methyl-1H-tetrazol-1-acetamide, prepared as described under A above, in 50 ml. of methylene chloride containing 0.8 g. of pyridine and maintained at a temperature of about 0° C. was added with stirring excess phosgene. After addition was complete, the reaction mixture was stirred for 10 minutes without further cooling. The clear solution obtained on reaction was evaporated to dryness at a temperature of about 30° C. under reduced pressure. The residue containing the reaction product was suspended in 50 ml. of dioxane, and 2.4 g. (15.2 mmole) of tetramethylguanidinium azide were added to the suspension. The mixture was heated for 2 hours at the reflux temperature and after stirring overnight at room temperature, the reaction mixture was concentrated to near dryness under reduced pressure. The concentrate was dissolved in 30 ml. of water forming a pale yellow solution from which the product crystallized as colorless needles. The product was filtered and 0.4 g. of the crystalline product melting at about 138° C. to about 140° C. were obtained. A second crop of 0.5 g. of the product melting at about 136° C. to about 139° C. was isolated from the filtrate.

The following analytical data were obtained for the crystalline product.

Elemental analysis calculated for $C_4H_5N_8Cl$: Theory: C, 23,95; H, 2.51; N, 55.86; Cl, 17.45. Found: C, 24.17; H, 2.75; N, 55.81; Cl, 17.85.

NMR (DMSO-$d_6$): δ 4.27 (s, 3H, N-$CH_3$), 6.33 (s, 2H, $CH_2$) ppm.

C. 1-(1-Methyl-1H-tetrazol-5-ylmethyl)-1H-tetrazol-5-thiol

To a suspension of 0.5 g. (2.5 mmole) of the 5-chloro-bis-tetrazole, prepared as described in B above, in 40 ml. of ethyl alcohol was added 0.6 g. of sodium hydrosulfide. The mixture was heated at the reflux temperature for 16 hours, was cooled to room temperature, and filtered. The filtrate was concentrated to near dryness under reduced pressure and 30 ml. of 5% hydrochloric acid were added. The acidified concentrate was extracted 3 times with 30 ml. portions of ethyl acetate, and the extracts were combined and washed with 5% hydrochloric acid, brine, and dried over sodium sulfate. The dried extract was concentrated to a small volume from which the crystalline product precipitated. The product was recrystallized from ethyl acetate-hexane, and there was obtained 0.3 g. of the product as nearly colorless crystals melting at about 190° C. to about 192° C.

The following analytical data were obtained for the crystalline product.

Elemental analysis calculated for $C_4H_6N_8S$: Theory: C, 24.24; H, 3.05; N, 56.53. Found: C, 24.21; H, 3.28; N, 56.43.

NMR (DMSO-$d_6$): δ 4.22 (s, 3H, $CH_3$), 5.95 (s, 2H, $CH_2$), 10.57 (broad s, 1H, SH).

The molecular weight as determined by mass spectrum was 198.

2-(1H-Tetrazole-5-ylmethyl)-tetrazole-5-thiol preparation

A. 5-Benzylthio-1H-tetrazole

A solution of 30 g. (0.33 mole) of thiosemicarbazide and 51 g. (0.40 mole) of benzyl chloride in 500 ml. of ethyl alcohol was heated at the reflux temperature for about 3.5 hours. After heating, the reaction mixture was evaporated to dryness under reduced pressure and the residue was dissolved in water. The solution was washed with ethyl acetate and was added to a solution of 25 g. (0.36 mole) of sodium nitrite in 50 ml. of water. The solution was stirred for 15 minutes and then ethyl acetate was added. The organic layer was separated and washed with water, brine, and was dried over sodium sulfate. The dried ethyl acetate solution was evaporated under reduced pressure, and the product obtained as a residue was washed with methylene chloride and recrystallized from ethyl acetate. There was obtained 21 g. of the product melting at about 134° C. to about 136° C.

The following elemental analysis was obtained for the product.

Elemental analysis calculated for $C_8H_8N_4S$: Theory: C, 49.98; H, 4.19; N, 29.14. Found: C, 49.81; H, 4.17; N, 28.95.

B. 1- and 2-Cyanomethyl-5-benzylthio-1H-tetrazole

A solution of 2.7 g. of potassium hydroxide in 5 ml. of methyl alcohol was added with stirring to a solution of 7.9 g. (0.041 M) of 5-benzylthio-1H-tetrazole in 25 ml. of methyl alcohol, and after stirring the solution for 15 minutes at room temperature, 3.4 g. (0.045 M) of chloroacetonitrile were added. The reaction mixture was heated at the reflux temperature for about 12 hours and the white solid which formed was filtered. The filtrate was concentrated in vacuo to an oily residue, and the residue dissolved in a mixture of diethyl ether and water. The ether layer was separated and washed with an aqueous solution of sodium bicarbonate, water, and with brine, and was dried and evaporated to dryness under reduced pressure. There were obtained 3.4 g. of a mixture of 1- and 2-cyanomethyl-5-benzylthio-1H-tetrazole as a reddish oil. The NMR spectrum of the oil showed it was a mixture containing approximately 50% of each of the isomers.

C.
5-Benzylthiol-2-(1H-tetrazol-5-ylmethyl)-2H-tetrazole

To 70 ml. of dry tetrahydrofuran cooled in an ice-ethanol bath were added in small portions 4.04 g. (0.03 mole) of anhydrous aluminum chloride. After addition was complete, 5.85 g. (0.09 mole) of finely ground sodium azide were added with stirring. After stirring the mixture for 5 minutes, a solution of 3.93 g. (0.017 mole) of the 1- and 2-cyanomethyl-5-benzylthio-tetrazole isomeric mixture in 20 ml. of dry tetrahydrofuran was added and the mixture heated at the reflux temperature for 24 hours. The reaction mixture was cooled in an ice-ethanol mixture and acidified by dropwise addition of 30 ml. of 20% hydrochloric acid. The acidified mixture was concentrated under reduced pressure to a volume of about 30 ml., and the concentrate was extracted with three 30 ml. portions of ethyl acetate. The extracts were combined, washed with brine, and dried over anhydrous sodium sulfate. The dried extract was evaporated under vacuum to dryness providing 4.5 g. (97% yield) of a mixture of the isomeric 5-benzylthio-1- and 2-(1H-tetrazole-5-ylmethyl)-1H- and 2H-tetrazoles as a tan oil. After standing for several days, crystals formed in the oil. The mixture was triturated with methylene chloride and filtered to provide 0.85 g. of cream colored crystals melting at about 115° C. to about 117° C. A second crop of crystals which weighed 0.2 g. was obtained from the filtrate.

The above preparation was repeated by reacting 7.1 g. of the isomeric 5-benzylthio-1- and 2-cyanomethyl-tetrazole with aluminum azide (formed as described above with 7.3 g. of aluminum chloride and 10.7 g. of sodium azide). After heating at the reflux temperature for 24 hours, the reaction mixture was acidified with 20% hydrochloric acid, evaporated to a volume of about 60 ml., extracted with ethyl acetate, the extract washed with brine, dried, and evaporated to dryness. The residue crystallized on standing. The cream colored crystals were suspended in methylene chloride and filtered to provide 3.5 g. of crystalline material. The filtrate was evaporated to dryness to provide 4.9 g. of orange oil.

The nmr spectrum of the crystalline product run in deuterated DMSO showed mainly one isomer, the 2-isomer, while the nmr spectrum of the oil showed mainly the 1-isomer.

D. 2-(1H-Tetrazole-5-ylmethyl)-2H-tetrazole-5-thiol

5-Benzylthio-2-(1H-tetrazole-5-ylmethyl)-2H-tetrazole, 175 mg., prepared as described above under part C, was dissolved in 40 ml. of distilled DMF and reduced at the mercury pool cathode (14 cm² Hg pool) with a platinum wire anode. The electrodes were separated by a glass frit. The electrolyte was tetraethylammonium perchlorate, 0.1 M in the DMF solution of the substrate. The electrolysis was carried out at $-2.7$ to $-2.85$ volts for 500 seconds and at $-2.80$ v. for about 630 seconds.

The reduction product mixture from the one-electron reduction was evaporated to dryness and the residue of product dissolved in ethyl acetate. The solution was washed three times with a 9:1 by volume mixture of a saturated solution of sodium chloride and 0.1 N hydrochloric acid and was dried over anhydrous magnesium sulfate. The dried solution was concentrated in vacuo and 111 mg. of the title compound precipitated from the concentrate. The product was filtered and dried.

EXAMPLE 1

7β-[dl-[Carboxy(4-hydroxyphenyl)acetyl]amino]-7α-methoxy-8-oxo-3-[[[1-(1H-tetrazol-5-ylmethyl)-1H-tetrazol-5-yl]thio]methyl]-5-oxa-1-azabicyclo[4.2.0]oct-2-ene-2-carboxylic acid To a solution of 1.33 g (1.83 mmole) of diphenylmethyl 7β-[dl-[3-methoxybenzylcarbonyl(4-hydroxyphenyl)acetyl]amino]-7α-methoxy-8-oxo-3-(chloromethyl)-5-oxa-1-azabicyclo[4.2.0]oct-2-ene-2-carboxylate of the formula

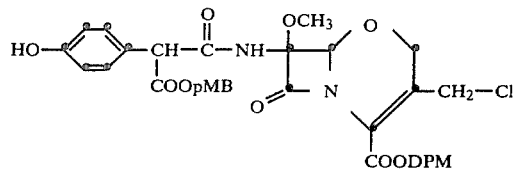

in 12 ml of methylene chloride containing 200 mg of tetra-n-butylammonium chloride was added at room temperature a solution of 368 mg (2 mmole) of 1-(1H-tetrazol-5-ylmethyl)-1H-tetrazol-5-thiol in 4 ml of 0.5 N sodium hydroxide and 4 ml of water. The two-phase reaction mixture was stirred at room temperature for 18 hours. The methylene chloride layer was separated and was washed with water, with brine, dried over sodium sulfate and evaporated to dryness under vacuum. There were obtained 1.33 g (83 percent yield) of 3-substituted diester of the formula

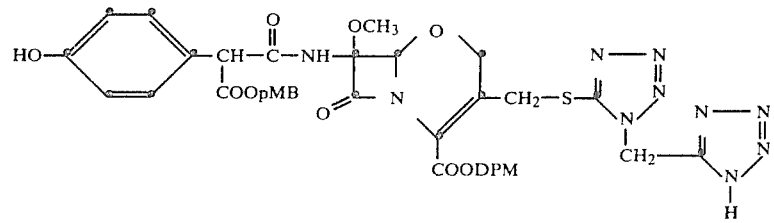

as a golden-colored foam.

The 3-substituted diester of the above formula was de-esterified as follows.

A solution of 1.16 g (1.3 mmole) of the diester in 6 ml of methylene chloride and 6 ml of nitromethane was cooled to a temperature of 0° C. To the cold was slowly added a solution of 950 mg of aluminum chloride in 6 ml of anisole and the reaction mixture was stirred at 0° C. for one hour and for 30 min. at room temperature. The reaction mixture was evaporated under reduced pressure to remove solvents and 20 ml of ethyl acetate, 20 ml of water and 0.5 ml of 20% hydrochloric acid were added to the residue of crude diacid. The mixture was stirred vigorously for 5 minutes and the solid diacid product which formed was filtered and washed with water. The crude diacid was sonicated in acetone-methyl alcohol, filtered, and the filtrate evaporated to dryness. There were obtained 187 mg of the crude diacid product as a gum.

The product was purified as follows. A solution of 185 mg. of the gum in 1.5 ml of methyl alcohol was injected onto a C18 Reverse Phase silica HPLC column and chromatographed at 250 psi with the eluent 6% acetonitrile—2% acetic acid—92% water. The chromatogram was monitored by UV. Multiple fractions were collected and fractions 21–46 containing the product were combined and evaporated to remove the acetonitrile. The aqueous concentrate was lyophilized and there were obtained 17 mg of the title compound as white solid. The product is represented by the formula

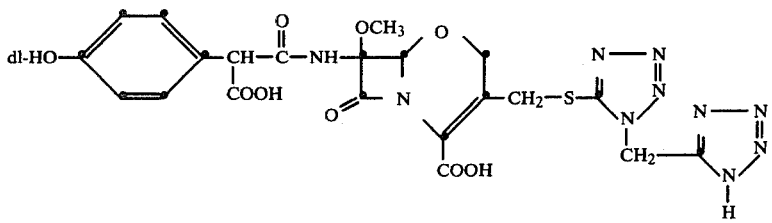

NMR (90 MHz, DMSOd$_6$; DMSO reference, 2.65 ppm) δ 3.56 (s, 7-methoxy H), 4.44 (s, 3'-methylene), 4.60 (m, methane H of malonamido side chain), 4.86 (s, C-2 methylene), 5.25 (s, C-6 H), 5.87 (s, methylene of bis-tetrazole), and 7.16 (m, p-hydroxyphenyl H) ppm.

EXAMPLE 2

7β-(2-Thienylacetylamino)-7α-methoxy-8-oxo-3-[[[1-(1H-tetrazol-5-ylmethyl)-1H-tetrazol-5-yl]thio]methyl]-5-oxa-1-azabicyclo[4.2.0]oct-2-ene-2-carboxylic acid 7β-(2-Thienylacetylamino)-7α-methoxy-8-oxo-3-[[[chloromethyl]thio]methyl]-5-oxa-1-azabicyclo[4.2.0]oct-2-ene-2-carboxylic acid 4-nitrobenzyl ester is dissolved in methylene chloride and tetra-n-butylammonium chloride is added. To the solution is added a solution of excess 1-(1H-tetrazol-5-ylmethyl)-1H-tetrazole-5-thiol in excess 0.05 N sodium hydroxide. The two-phase reaction mixture is stirred vigorously for about eight hours at room temperature. The organic phase is separated and washed with water and brine and is dried and evaporated to provide the title compound as the 4-nitrobenzyl ester. The ester group is removed with zinc and acetic acid in tetrahydrofuran to provide the title compound.

EXAMPLE 3

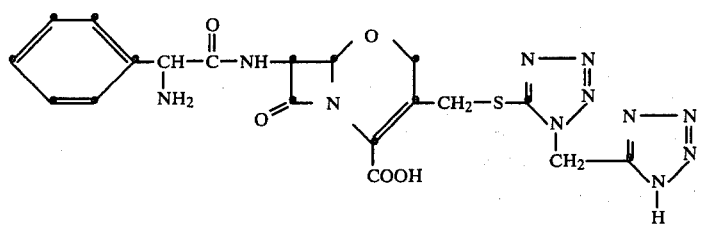

7β-[D-[Amino(phenyl)acetyl]amino]-8-oxo-3-[[[1-(1H-tetrazol-5-ylmethyl)-1H-tetrazol-5-yl]thio]methyl]-5-oxa-1-azabicyclo[4.2.0]oct-2-ene-2-carboxylic acid The title compound is prepared by acylating 7β-amino-8-oxo-3-[[[1-(1H-tetrazol-5-ylmethyl)-1H-tetrazol-5-yl]thio]methyl]-5-oxa-1-azabicyclo[4.2.0]-oct-2-ene-2-carboxylic acid 4-nitrobenzyl ester with the amino-protected mixed anhydride derivative of D-phenylglycine represented by the formula,

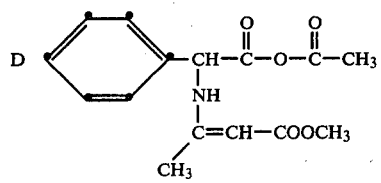

wherein the amino group is protected with the enamine formed with methyl acetoacetate and the mixed anhydride is formed by reacting the enamine protected phenylglycine sodium salt with methyl chloroformate.

The acylation is carried out under non-aqueous conditions in acetonitrile and the aminoprotected and esterified acylation product is de-esterified and de-protected at the amino group to form the title compound by treating the protected acylation product with zinc and acetic acid under aqueous conditions.

EXAMPLE 4

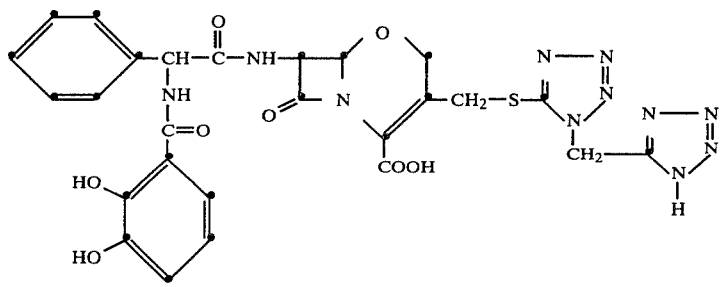

7β-[D-[2,3-Dihydroxybenzamido(phenyl)acetyl-]amino]-8-oxo-3-[[[1-(1H-tetrazol-5-ylmethyl)-1H-tetrazol-5-yl]-thio]methyl]-5-oxa-1-azabicyclo[4.2.0]oct-2-ene-2-carboxylic acid The title compound is prepared by acylating the 7β-(D-phenylglycylamino)-1-oxa-β-lactam compound of Example 3 with the active ester of 2,3-dihydroxybenzoic acid formed with hydroxybenzotriazole (HBT). The acylation is carried out under non-aqueous conditions in acetonitrile or tetrahydrofuran.

EXAMPLE 5

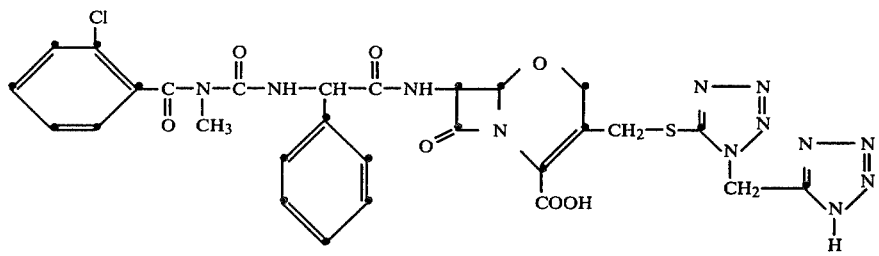

The compound of the above formula is prepared by reacting the 7β-(D-phenylglycyamino)-1-oxa-β-lactam compound, obtained as described in Example 3, with N-methyl-N-chlorocarbonyl-2-chlorobenzamide in tetrahydrofuran containing dimethylformamide as a co-solvent and pyridine as the hydrogen chloride acceptor.

EXAMPLE 6

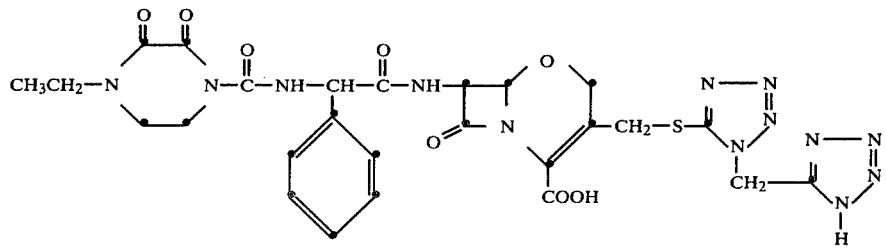

7β-[D-[4-Ethylpiperazin-2,3-dione-1-ylcarbonylamino--(phenyl)acetyl]amino]-8-oxo-3-[[[1-(1H-tetrazol-5-ylmethyl)-1H-tetrazol-5-yl]thio]methyl]-5-oxa-1-azabicyclo[4.2.0]oct-2-ene-2-carboxylic acid The title compound is prepared by acylating 7β-(D-phenylglycylamino)-1-oxa-β-lactam compound of Example 3 with 4-ethylpiperazin-2,3-dione-1-ylcarbonyl chloride in acetonitrile in the presence of propylene oxide.

I claim:

1. A compound of the formula

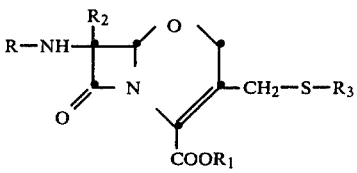

wherein R is hydrogen or an acyl group of the formula $$R°-\overset{O}{\underset{\|}{C}}-$$

wherein R° is an aryl or aralkyl group of the formula $$R^1-(CH_2)_m,$$

wherein $R^1$ is phenyl or phenyl substituted by halogen, hydroxy, amino, acetamido, $C_1$-$C_4$ alkyl, $C_1$-$C_4$ alkoxy, cyano, carboxy, carboxamido, carboxymethyl, $C_1$-$C_4$ alkoxycarbonylmethyl, hydroxymethyl, or aminomethyl;

or $R^1$ is a di- or tri-substituted phenyl group of the formula

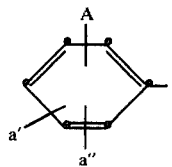

wherein each of a, a', and a" are independently hydrogen, halogen, hydroxy, $C_1-C_4$ alkyl or $C_1-C_4$ alkoxy; and
n is 0 or 1;
or $R°$ is an aryloxymethyl or arylthiomethyl group of the formula $R^1-(Z)-CH_2-$ wherein $R^1$ has the same meanings as defined above, and Z is O or S;
or $R°$ is a heterocyclic methyl group of the formula $R^2-CH_2-$ wherein $R^2$ is thienyl, furyl, 1H-tetrazol-1-yl, 1H-tetrazol-5-yl,

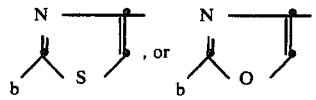

wherein each b is hydrogen, amino, protectedamino, $C_1-C_3$ alkyl or phenyl;
or $R°$ is a group of the formula

wherein $R^3$ is $R^1$ as defined above and in addition 1,4-cyclohexadienyl, thienyl or furyl, and Q is hydroxy, carboxy, sulfo, or amino;
or $R°$ is an oximino substituted group represented by the formula

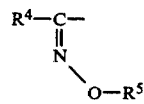

wherein $R^4$ is $R^1$ as defined above and in addition thienyl, furyl, or

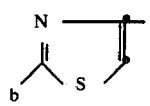

wherein b has the same meanings as defined above and $R^5$ is hydrogen, or $C_1-C_4$ alkyl;
or $R°$ is a group of the formula

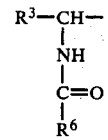

wherein $R^3$ is as defined above and $R^6$ is phenyl substituted by 1-3 hydroxy groups or pyridyl substituted with from 1-3 hydroxy groups;
or $R^6$ is a group of the formula

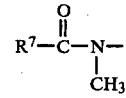

wherein $R^7$ is $C_1-C_4$ alkylamino, phenyl, chlorophenyl, furyl, styrryl, chlorostyrryl, or nitrostyrryl;
or $R^6$ is a group of the formula

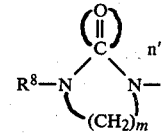

wherein n' is 1 or 2 and m is 2 or 3 with the limitation that when n' is 2, m is 2; and $R^8$ is hydrogen, $C_1-C_3$ alkyl, $C_2-C_4$ alkanoyl, or $C_1-C_3$ alkylsulfonyl;
$R_1$ is hydrogen or a carboxy-protecting group;
$R_2$ is hydrogen or methoxy;
$R_3$ is a bis-tetrazolemethyl group of the formula

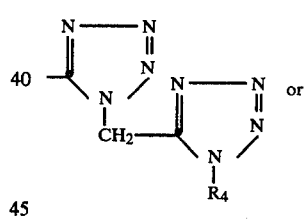

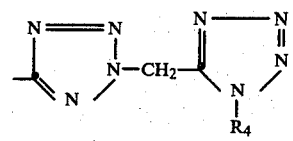

wherein each $R_4$ is hydrogen or $C_1-C_3$ alkyl; and when $R_1$ is hydrogen, the pharmaceutically acceptable non-toxic salts thereof.

2. The compound of claim 1 wherein R is an acyl group of the formula

3. The compound of claim 2 wherein $R°$ is a aryl or aralkyl group of the formula

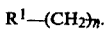

4. The compound of claim 2 wherein $R°$ is a group of the formula

5. The compound of claim 2 wherein R° is a heterocyclic methyl group of the formula $$R^2-CH_2-.$$

6. The compound of claim 5 wherein $R^2$ is thienyl.

7. The compound of claim 2 wherein R° is a group of the formula $$R^3-\underset{Q}{\underset{|}{CH}}-.$$

8. The compound of claim 7 wherein Q is carboxy.

9. The compound of claim 8 wherein $R^3$ is phenyl or substituted phenyl.

10. The compound of claim 9 wherein $R_3$ is a bis-tetrazole methyl group of the formula

[structure: bis-tetrazole methyl group with $R_4$]

11. The compound of claim 10 wherein $R_2$ is methoxy, and $R^3$ is hydroxyphenyl.

12. The compound of claim 11 wherein $R_4$ is hydrogen.

13. The compound of claim 12 of the formula

[structure of the compound]

14. The compound of claim 2 wherein R° is an oximino substituted group of the formula $$R^4-\underset{\underset{\underset{O-R^5}{|}}{N}}{\overset{\|}{C}}-.$$

15. The compound of claim 14 wherein $R^4$ is

[thiazole structure with b]

16. The compound of claim 15 wherein $R_3$ is

[tetrazole structure]

17. The compound of claim 2 wherein R° is a group of the formula $$R^3-\underset{\underset{\underset{R^6}{|}}{\underset{C=O}{|}}}{\underset{NH}{\underset{|}{CH}}}-.$$

18. The compound of claim 17 wherein $R^6$ is

[two structures: dihydroxyphenyl or hydroxypyridyl]

19. The compound of claim 18 wherein $R^6$ is a group of the formula $$R^7-\underset{\underset{CH_3}{|}}{\overset{\overset{O}{\|}}{C}}-\underset{}{N}-.$$

20. The compound of claim 19 wherein $R^7$ is phenyl, chlorophenyl, or furyl.

21. The compound of claim 19 wherein $R^7$ is $C_1-C_4$ alkylamino.

22. The compound of claim 21 wherein $R^7$ is methylamino.

23. The compound of claim 17 wherein $R^6$ is a group of the formula

[cyclic structure with $R^8-N$, $(CH_2)_m$, and $C_{n'}=O$]

24. The compound of claim 23, wherein $n'$ is 1 and $m$ is 2, of the formula

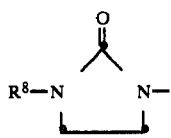
and $R^8$ is H, or methylsulfonyl.
25. The compound of claim 23, wherein n' is 2 and m is 2, of the formula
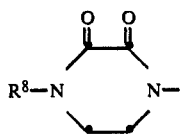
wherein $R^8$ is ethyl.
26. The pharmaceutical formulation suitable for antibiotic use comprising an effective amount of a compound of claim 1 and a pharmaceutically acceptable carrier.
27. The formulation of claim 26 where, in the antibiotic, $R_3$ is a group of the formula
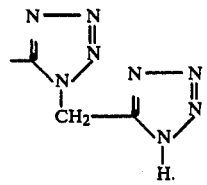
* * * * *